(12) United States Patent
Leal et al.

(10) Patent No.: US 11,124,470 B2
(45) Date of Patent: Sep. 21, 2021

(54) SYSTEMS AND METHODS OF PRODUCING METHYL TERTIARY BUTYL ETHER AND PROPYLENE

(71) Applicant: SABIC Global Technologies B.V., Bergen op Zoom (NL)

(72) Inventors: Guillermo Leal, Riyadh (SA); Mohammed Bismillah Ansari, Riyadh (SA); Vijay Dinkar Bodas, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 73 days.

(21) Appl. No.: 16/496,511

(22) PCT Filed: Mar. 29, 2018

(86) PCT No.: PCT/IB2018/052203
§ 371 (c)(1),
(2) Date: Sep. 23, 2019

(87) PCT Pub. No.: WO2018/185628
PCT Pub. Date: Oct. 11, 2018

(65) Prior Publication Data
US 2021/0002196 A1 Jan. 7, 2021

Related U.S. Application Data

(60) Provisional application No. 62/480,687, filed on Apr. 3, 2017.

(51) Int. Cl.
| | | |
|---|---|---|
| *C07C 41/06* | (2006.01) | |
| *C07C 5/05* | (2006.01) | |
| *C07C 6/00* | (2006.01) | |
| *C07C 6/04* | (2006.01) | |
| *C07C 7/04* | (2006.01) | |
| *C07C 7/163* | (2006.01) | |
| *C07C 11/06* | (2006.01) | |
| *C07C 43/04* | (2006.01) | |

(52) U.S. Cl.
CPC .............. *C07C 41/06* (2013.01); *C07C 5/05* (2013.01); *C07C 6/04* (2013.01); *C07C 7/04* (2013.01); *C07C 7/163* (2013.01); *C07C 11/06* (2013.01); *C07C 43/046* (2013.01)

(58) Field of Classification Search
CPC .. C07C 41/06; C07C 5/05; C07C 6/04; C07C 11/06
See application file for complete search history.

(56) References Cited

U.S. PATENT DOCUMENTS

| | | | |
|---|---|---|---|
| 5,300,718 A | 4/1994 | McCaulley | 585/324 |
| 5,523,502 A | 6/1996 | Rubin | 585/324 |
| 5,670,703 A | 9/1997 | Barendregt et al. | 585/324 |
| 5,898,091 A | 4/1999 | Chodorge et al. | 585/647 |
| 6,159,433 A | 12/2000 | Chodorge et al. | 422/189 |
| 6,977,318 B2 | 12/2005 | Bridges | 585/324 |
| 7,220,886 B2 * | 5/2007 | Podrebarac | C07C 6/04 585/324 |
| 2006/0089517 A1 | 4/2006 | Podrebarac et al. | 585/643 |
| 2009/0112032 A1 | 4/2009 | Eng | 585/324 |
| 2009/0112039 A1 | 4/2009 | Eng | 585/651 |
| 2013/0066032 A1 | 3/2013 | Chewter et al. | 526/351 |
| 2016/0326079 A1* | 11/2016 | Leal | C07C 41/06 |

FOREIGN PATENT DOCUMENTS

| | | |
|---|---|---|
| CN | 101255086 | 9/2010 |
| CN | 101555197 | 1/2013 |
| CN | 101492335 | 7/2013 |
| CN | 103382147 | 11/2013 |

OTHER PUBLICATIONS

UOP C4 Process Brochure, accessed online on Mar. 21, 2017. https://www.uop.com/wp-content/uploads/2012/12/Crude_C4_Processing-900x400.jpg.
Torck, C. H. "Upgrading Ethylene Plant Coproducts." World Petroleum Congress, [11]2 (1994), 8 pages.
International Search Report and Written Opinion from PCT/IB2018/052203 dated Jun. 19, 2018, 10 pages.

* cited by examiner

*Primary Examiner* — Sikarl A Witherspoon
(74) *Attorney, Agent, or Firm* — Norton Rose Fulbright US LLP

(57) ABSTRACT

A method of producing methyl tertiary butyl ether (MTBE) and propylene is disclosed. The method involves the use of a crude C4 stream and the integration of a MTBE synthesis process and a cracking process. The method may include processing a byproduct stream from an MTBE synthesis unit to produce high purity olefin streams for an olefins conversion technology unit.

20 Claims, 2 Drawing Sheets

SYSTEMS AND METHODS OF PRODUCING METHYL TERTIARY BUTYL ETHER AND PROPYLENE

CROSS REFERENCE TO RELATED APPLICATIONS

This application is a national phase application under 35 U.S.C. § 371 of International Application No. PCT/IB2018/052203 filed Mar. 29, 2018, which claims priority to U.S. Provisional Patent Application No. 62/480,687 filed Apr. 3, 2017. The entire contents of each of the above-referenced disclosures is specifically incorporated by reference herein without disclaimer.

FIELD OF INVENTION

The present invention generally relates to the production of methyl tertiary butyl ether (MTBE) and propylene. Specifically the present invention relates to the utilization of crude $C_4$ streams in the production of MTBE and propylene.

BACKGROUND OF THE INVENTION

MTBE is used as a gasoline blending component. Typically, MTBE may be made by reacting isobutylene with methanol. The isobutylene for the reaction is usually obtained from a crude $C_4$ stream. A crude $C_4$ stream is a byproduct stream produced in a cracking process to produce olefins. The crude $C_4$ stream is usually obtained from the steam cracking of hydrocarbons to produce ethylene. Typically, materials that make up the crude $C_4$ stream have similar boiling points; thus extracting any one of the various components of the crude $C_4$ stream can be difficult and expensive.

Propylene serves as a building block for other petrochemical products and may be made by different processes. One of those processes, olefins conversion technology (OCT), involve metathesis and isomerization of hydrocarbons to form the propylene. Another of the processes involve steam cracking larger hydrocarbons to form the propylene. The steam cracking process, in addition to producing propylene, may produce n-butane and isobutane, which are both usually recycled to the transfer hydrogenation unit (THU) of the steam cracker.

Conventionally, the MTBE production process and the OCT process are not integrated with the steam cracking process. Moreover, the stream from the steam cracker that includes the n-butane and isobutane is not pure enough to be utilized in MTBE production.

BRIEF SUMMARY OF THE INVENTION

A method has been discovered in which purified 1-butene and 2-butene streams can be obtained from a stream that emanates from a steam cracker and that includes primarily normal butane (n-butane) and isobutane collectively. The n-butane and isobutane are inert in certain processes, such as butadiene production process, MTBE production process, 1-butene production process, and OCT process (metathesis). Accommodating the n-butane and isobutane volumes from the steam cracker in these processes, when they do not help in achieving the objective of those processes, would have a direct effect in the operational efficiency, technical efficiency, and the capital expenditure required for these processes. Thus, in embodiments of the invention, the materials that are inert to the processes are removed from the streams entering one or more of those processes. In this way, capital expenditure for the equipment and the efficiency of the processes are kept at optimal levels.

Embodiments of the invention include a method of producing methyl tertiary butyl ether (MTBE) and propylene. The method may include flowing a crude $C_4$ stream comprising butadiene, isobutylene, 2-butene, 1-butene, acetylene, isobutane, and n-butane to a selective hydrogenation unit and hydrogenating the butadiene in the selective hydrogenation unit to form additional 1-butene and additional 2-butene. The additional 1-butene, the additional 2-butene and unreacted material of the crude $C_4$ stream are included in effluent of the selective hydrogenation unit. The method may further include flowing the effluent of the selective hydrogenation unit to a MTBE synthesis unit and reacting, in the MTBE synthesis unit, the isobutylene from the crude $C_4$ stream with methanol (MeOH) to produce the MTBE. The method may further include flowing, from the MTBE synthesis unit, a byproduct stream comprising 1-butene, isobutane, 2-butene, and n-butane to a processing unit, and processing, in the processing unit, the byproduct stream to produce a first stream comprising primarily 1-butene and a second stream comprising primarily 2-butene. The method may further include flowing the second stream comprising primarily 2-butene to an olefins conversion technology unit and reacting the 2-butene with ethylene to produce propylene.

Embodiments of the invention include a method of producing methyl tertiary butyl ether (MTBE) and propylene. The method may include flowing a crude $C_4$ stream comprising butadiene, isobutylene, 2-butene, 1-butene, acetylene, isobutane, and n-butane to a selective hydrogenation unit and hydrogenating the butadiene in the selective hydrogenation unit to form additional 1-butene and additional 2-butene. The additional 1-butene, the additional 2-butene and unreacted material of the crude $C_4$ stream are included in effluent of the selective hydrogenation unit. The method may further include flowing the effluent of the selective hydrogenation unit to a MTBE synthesis unit and reacting, in the MTBE synthesis unit, the isobutylene from the crude $C_4$ stream with methanol (MeOH) to produce the MTBE. The method may further include flowing, from the MTBE synthesis unit, a byproduct stream comprising 1-butene, isobutane, 2-butene, and n-butane to a processing unit. Further, the method may include distilling, in a distillation column of the processing unit, the byproduct stream to form a first intermediate stream comprising primarily 1-butene and isobutane and a second intermediate stream comprising primarily 2-butene and n-butane. The method may then include hydro-isomerizing of the 1-butene in the first intermediate stream to produce a stream comprising primarily 2-butene and isobutane and separating the stream comprising primarily 2-butene and isobutane into a stream comprising primarily 2-butene and a stream comprising primarily isobutane. The method may further include isomerization of the 2-butene of the second intermediate stream to form a stream comprising primarily 1-butene and n-butane and separating the stream comprising primarily 1-butene and n-butane to form a stream comprising primarily 1-butene and a stream comprising primarily n-butane. The method may include flowing the stream comprising primarily 2-butene and the stream comprising primarily 1-butene to an olefins conversion technology unit, converting 1-butene of the stream comprising primarily 1-butene to 2-butene in the olefins conversion technology unit, and reacting the 2-butene in the olefins conversion technology unit with ethylene to produce propylene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention at least the nineteen preferred embodiments are described. Embodiment 1 is a method of producing methyl tertiary butyl ether (MTBE) and propylene. The method includes the steps of flowing a crude C4 stream containing butadiene, isobutylene, 2-butene, 1-butene, acetylene, isobutane, and n-butane to a selective hydrogenation unit; hydrogenating the butadiene in the selective hydrogenation unit to form additional 1-butene and additional 2-butene, wherein the additional 1-butene and the additional 2-butene and unreacted material of the crude C4 stream is included in effluent of the selective hydrogenation unit; flowing the effluent of the selective hydrogenation unit to a MTBE synthesis unit; reacting, in the MTBE synthesis unit, the isobutylene from the crude C4 stream with methanol (MeOH) to produce the MTBE, flowing, from the MTBE synthesis unit, a byproduct stream containing 1-butene, isobutane, 2-butene, and n-butane to a processing unit; processing, in the processing unit, the byproduct stream to produce a first stream containing primarily 1-butene and a second stream containing primarily 2-butene; flowing the second stream containing primarily 2-butene to an olefins conversion technology unit; and reacting the 2-butene with ethylene to produce propylene. Embodiment 2 is the method of embodiment 1 further including the step of hydrogenating the butadiene in the selective hydrogenation unit to form additional isobutane and additional n-butane. Embodiment 3 is the method of any of embodiments 1 and 2, wherein processing, in the processing unit includes the step of distilling, in a distillation column of the processing unit, the byproduct stream to form a first intermediate stream containing primarily 1-butene and isobutane, collectively, and a second intermediate stream containing primarily 2-butene and n-butane, collectively. Embodiment 4 is the method of embodiment 3, further including the step of processing the first intermediate stream to produce a stream containing primarily 2-butene and a stream containing primarily isobutane. Embodiment 5 is the method of embodiment 4, wherein the processing of the first intermediate stream includes the steps of hydro-isomerizing of the 1-butene in the first intermediate stream to produce a stream containing primarily 2-butene and isobutane, collectively; and separating the stream containing primarily 2-butene and isobutane into the stream containing primarily 2-butene and the stream containing primarily isobutane. Embodiment 6 is the method of embodiment 5, further including the step of flowing the stream containing primarily 2-butene to the olefins conversion technology unit. Embodiment 7 is the method of any of embodiments 3 to 6, further including the step of processing the second intermediate stream to form a stream containing primarily 1-butene and a stream containing primarily n-butane. Embodiment 8 is the method of embodiment 7, wherein the processing the second intermediate stream includes the steps of isomerizing the 2-butene of the second intermediate stream to form a stream containing primarily 1-butene and n-butane, collectively; and separating the stream containing primarily 1-butene and n-butane to form the stream containing primarily 1-butene and the stream containing primarily n-butane. Embodiment 9 is the method of embodiment 8, further including the step of flowing the stream containing primarily 1-butene to the olefins conversion technology unit; converting 1-butene of the stream containing primarily 1-butene to 2-butene in the olefins conversion technology unit. Embodiment 10 is the method of any of embodiments 1 to 9, wherein the acetylene in the crude C4 stream contains ethyl acetylene and vinyl acetylene. Embodiment 11 is the method of any of embodiments 1 to 10, wherein the butadiene contains 1,3-butadiene and 1,2-butadiene. Embodiment 12 is the method of any of embodiments 1 to 11, wherein the 2-butene contains cis-2-butene and trans-2-butene. Embodiment 13 is the method of any of embodiments 1 to 12, wherein the MTBE synthesis unit contains a separation unit. Embodiment 14 is the method of any of embodiments 1 to 13, wherein the crude C4 stream is at least a portion of effluent from a fluid catalytic cracking unit or steam cracking unit. Embodiment 15 is the method of embodiment 14 wherein the stream containing primarily isobutane is used as feedstock for a selection from the group consisting of: (1) a dehydrogenation unit of the MTBE synthesis unit to produce additional isobutylene and (2) a transfer hydrogenation unit (THU) of the steam cracking unit to produce ethylene and propylene. Embodiment 16 is the method of embodiment 15, wherein the additional isobutylene is used to produce MTBE. Embodiment 17 is the method of embodiment 14, wherein the stream containing primarily n-butane is used as feedstock for a selection from the list consisting of: (1) an isomerization unit of the MTBE synthesis unit to produce more isobutane, (2) a transfer hydrogenation unit (THU) of the steam cracking unit to produce ethylene and propylene. Embodiment 18 is the method of embodiment 17, wherein the more isobutane is dehydrogenated to produce more isobutylene and the more isobutylene is used to produce MTBE. Embodiment 19 is the method of any of embodiments 2 to 18, wherein conversion of butadiene to other hydrocarbons in the selective hydrogenation unit is in a range of 88 wt. % to 92 wt. %.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1:
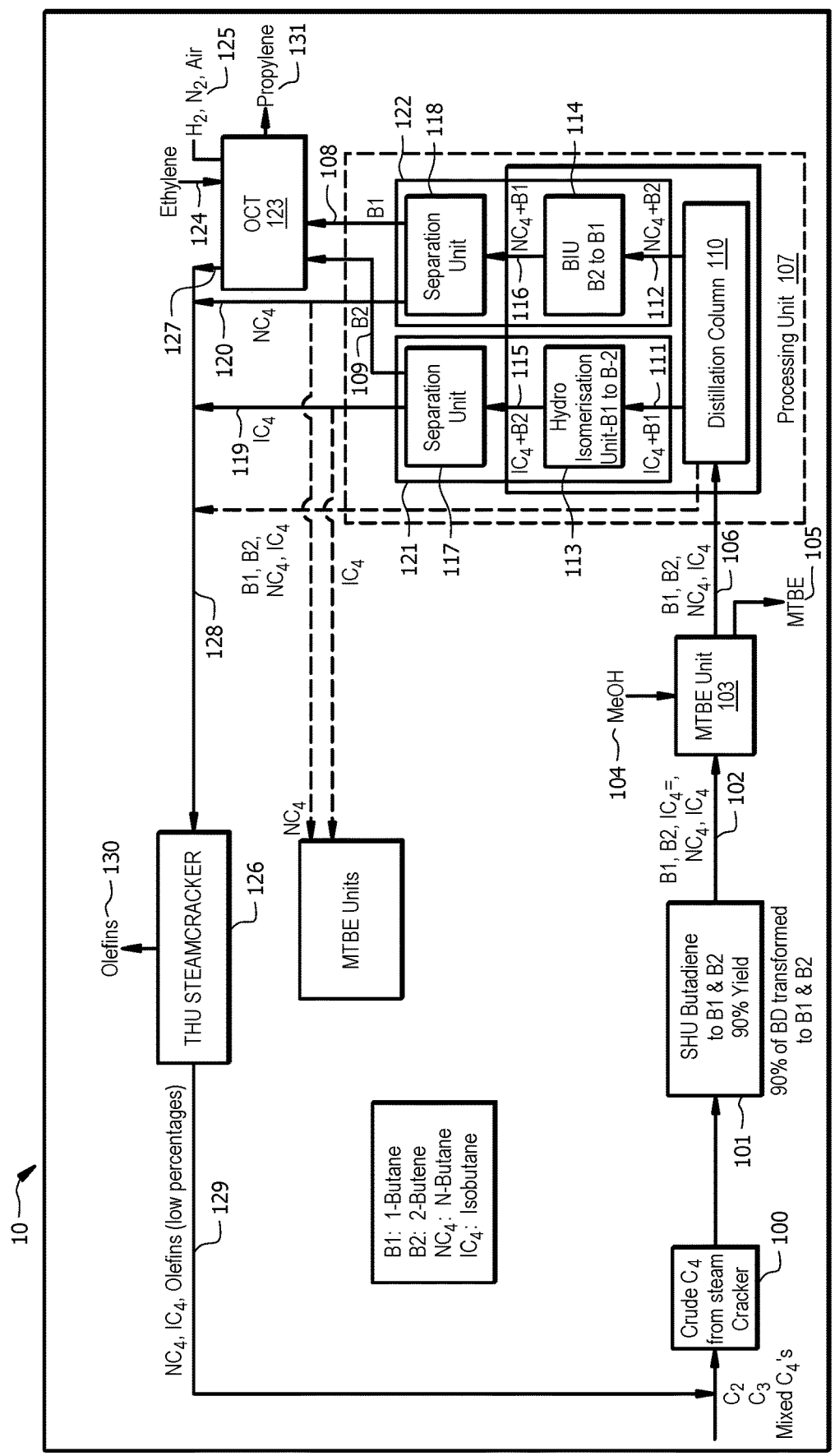
FIG. 1 shows a system for producing methyl tertiary butyl ether (MTBE) and propylene, according to embodiments of the invention.

A method has been discovered in which purified 1-butene and 2-butene streams can be obtained from a stream that emanates from a steam cracker and that includes primarily normal butane (n-butane) and isobutane, collectively. Embodiments of the invention include a method of producing methyl tertiary butyl ether (MTBE) and propylene. The method may first involve converting at least some of the butadiene to 1-butene and 2-butene. This may be done by flowing a crude $C_4$ stream comprising butadiene, isobutylene, 2-butene, 1-butene, acetylene, isobutane, and n-butane to a selective hydrogenation unit (which comprises a hydrogenation reactor) and hydrogenating the butadiene in the selective hydrogenation unit to form additional 1-butene and additional 2-butene. The additional 1-butene and the additional 2-butene and unreacted material of the crude $C_4$ stream are included in effluent of the selective hydrogenation unit. The method may further include removing most of the isobutylene by using it to produce MTBE. This may be done by flowing the effluent of the selective hydrogenation unit to a MTBE synthesis unit (which comprises an MTBE synthesis reactor) and reacting, in the MTBE synthesis unit, the isobutylene from the crude $C_4$ stream with methanol (MeOH) to produce the MTBE. The method may further include flowing, from the MTBE synthesis unit, a byproduct stream comprising 1-butene, isobutane, 2-butene, and n-butane to a processing unit.

Further, the method may include separating the byproduct stream into different streams. This separating may involve distilling, in a distillation column of the processing unit, the byproduct stream to form a first intermediate stream comprising primarily 1-butene and isobutane, collectively, and a second intermediate stream comprising primarily 2-butene and n-butane, collectively. The first stream and the second stream may undergo separate processes, based on the composition of these streams, to produce feedstock for an OTC unit that produces propylene. The method may then include hydro-isomerizing of the 1-butene in the first intermediate stream to produce a stream comprising primarily 2-butene and isobutane, collectively, and separating the stream comprising primarily 2-butene and isobutane into a stream comprising primarily 2-butene and a stream comprising primarily isobutane. The method may further include isomerization of the 2-butene of the second intermediate stream to form a stream comprising primarily 1-butene and n-butane, collectively, and separating the stream comprising primarily 1-butene and n-butane to form a stream comprising primarily 1-butene and a stream comprising primarily n-butane. The method may include flowing the stream comprising primarily 2-butene and the stream comprising primarily 1-butene to an olefins conversion technology unit, converting 1-butene of the stream comprising primarily 1-butene to 2-butene in the olefins conversion technology unit, and reacting the 2-butene in the olefins conversion technology unit with ethylene to produce propylene.

Figure 2:
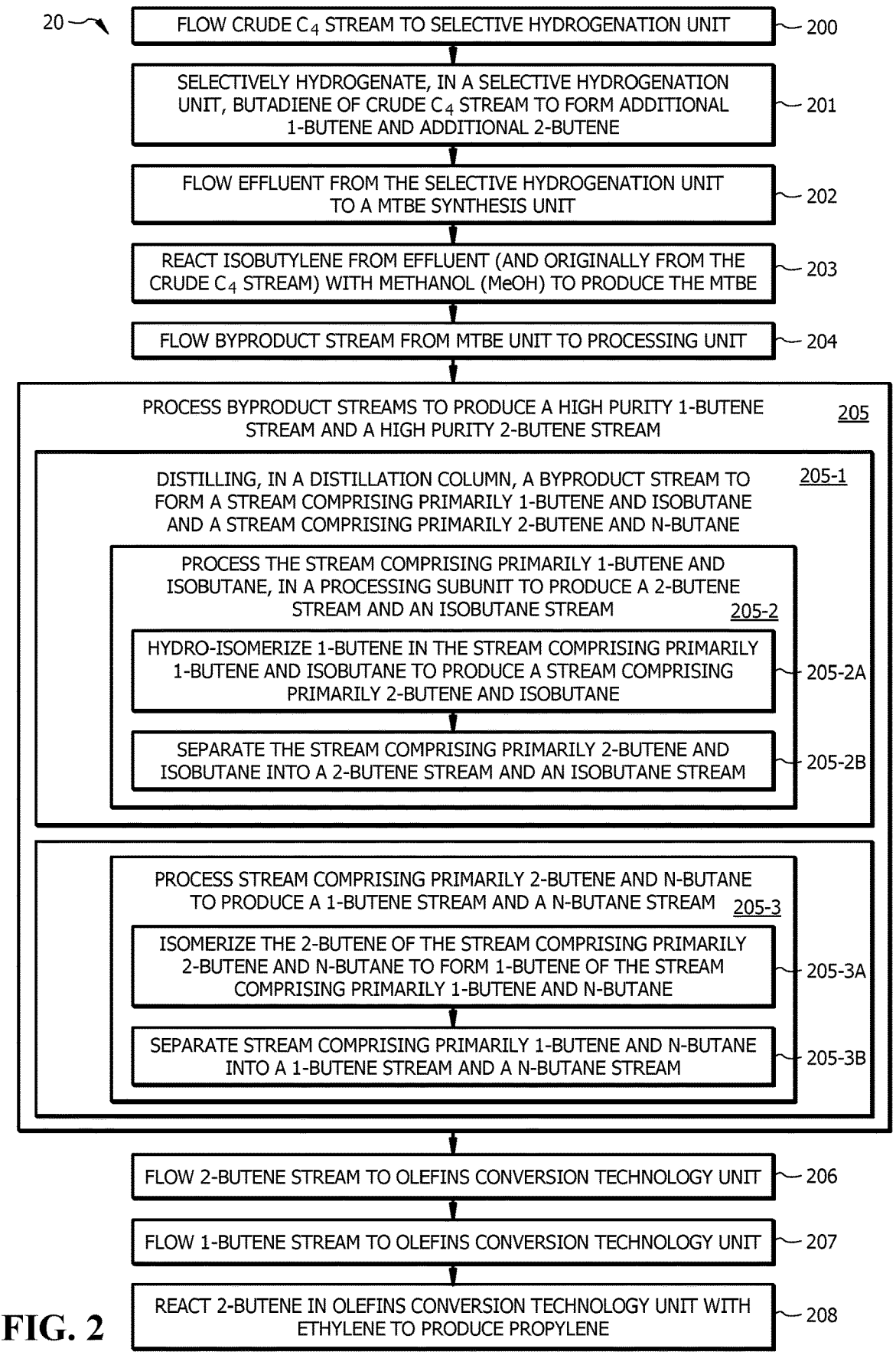
FIG. 2 shows a method for producing methyl tertiary butyl ether (MTBE) and propylene, according to embodiments of the invention.

FIG. 1 shows system 10 for producing methyl tertiary butyl ether (MTBE) and propylene, according to embodiments of the invention. FIG. 2 shows method 20 for producing methyl tertiary butyl ether (MTBE) and propylene, according to embodiments of the invention. Method 20 may be implemented using system 10.

Method 20 may begin at block 200, which involves flowing crude $C_4$ stream 100, comprising butadiene, isobutylene, 2-butene, 1-butene, acetylene, isobutane, and n-butane to selective hydrogenation unit 101. In embodiments of the invention, crude $C_4$ stream 100 is at least a portion of effluent from a fluid catalytic cracking unit or steam cracking unit. In embodiments of the invention, crude $C_4$ stream 100 comprises 0.01 to 50 wt. % butadiene, 0.01 to 50 wt. % isobutylene, 0.01 to 15 wt. % 2-butene, 0.01 to 15 wt. % 1-butene, 0.01 to 0.2 wt. % acetylene, 0.01 to 25 wt. % isobutane, and 0.01 to 50 wt. % n-butane. In embodiments of the invention, the acetylene in crude $C_4$ stream 100 comprises ethyl acetylene and vinyl acetylene. Further, in embodiments of the invention, the butadiene in crude $C_4$ stream 100 may comprise 1,3-butadiene and 1,2-butadiene. The 2-butene in crude $C_4$ stream 100, in embodiments of the invention, comprises cis-2-butene and trans-2-butene.

Block 201 may involve selectively hydrogenating the butadiene in selective hydrogenation unit 101 to form additional 1-butene and additional 2-butene. In embodiments of the invention, the reaction conditions in selective hydrogenation unit 101 include a temperature in the range 40 to 120° C., a pressure in the range 5 to 50 bar, and a gas hourly space velocity in the range 0.1 to 30 $hr^{-1}$. The additional 1-butene, the additional 2-butene, and unreacted material of crude $C_4$ stream 100, according to embodiments of the invention, are included in effluent 102 from selective hydrogenation unit 101. Block 201 may also involve, in embodiments of the invention, selectively hydrogenating the butadiene in selective hydrogenation unit 101 to form additional isobutane and additional n-butane. In embodiments of the invention, the conversion rate of the butadiene to the additional 1-butene and the additional 2-butene is 88 wt. % to 92 wt. %. In embodiments of the invention, effluent 102 comprises 0.001 to 0.01 wt. % butadiene, 0.01 to 15 wt. % isobutylene, 0.01 to 50 wt. % 2-butene, 0.01 to 50 wt. % 1-butene, 0.0001 to 0.01 wt. % acetylene, 0.01 to 50 wt. % isobutane, and 0.01 to 50 wt. % n-butane.

At block 202, effluent 102 from selective hydrogenation unit 101 is flowed to MTBE synthesis unit 103. In MTBE synthesis unit 103, block 203 is carried out, which involves reacting isobutylene from effluent 102 (and originally from the crude $C_4$ stream 100) with methanol (MeOH) 104 to produce the MTBE 105.

In embodiments of the invention, MTBE synthesis unit 103 includes a separation unit for separating MTBE 105 and byproduct stream 106. Block 204 involves flowing byproduct stream 106, which may comprise 1-butene, isobutane, 2-butene, and n-butane, from MTBE synthesis unit 103 to processing unit 107. In embodiments of the invention, byproduct stream 106 comprises 0.01 to 45 wt. % 2-butene, 0.01 to 45 wt. % 1-butene, 0.01 to 50 wt. % isobutane, and 0.01 to 50 wt. % n-butane.

Processing unit 107, as a whole, may be adapted to carry out block 205, which involves processing byproduct stream 106 to produce 1-butene stream 108 (a high purity stream), comprising primarily 1-butene, and 2-butene stream 109 (a high purity stream), comprising primarily 2-butene. Process unit 107 may include various processing components for carrying out the processing of block 204.

For example, method 20 may include, at block 205-1, distilling, in distillation column 110 (of processing unit 107) byproduct stream 106 to form stream 111 comprising primarily 1-butene and isobutane, collectively, and stream 112 comprising primarily 2-butene and n-butane, collectively. In embodiments of the invention, stream 111 comprises 0.01 to 70 wt. % 1-butene and 0 to 50 wt. % isobutane. In embodiments of the invention, stream 112 comprises 0.01 to 70 wt. % 2-butene and 0.01 to 50 wt. % isobutane.

At block 205-2, stream 111 may be processed, in processing subunit 121 to produce 2-butene stream 109, which comprises primarily 2-butene and stream 119 (a high purity stream) that comprises primarily isobutane. In embodiments of the invention, stream 109 comprises 90 to 99.9 wt. % 2-butene. In embodiments of the invention, stream 119 comprises 90 to 99.9 wt. % isobutane.

Processing subunit 121 may comprise hydro-isomerization unit 113 and separation unit 117. Hydro-isomerization unit 113 may be used to implement block 205-2A, which involves hydro-isomerizing of 1-butene in stream 111 to produce stream 115, which comprises primarily 2-butene and isobutane, collectively. In embodiments of the invention, the reaction conditions in hydro-isomerization unit 113 include a temperature in the range 110 to 300° C., a pressure in the range 15 to 30 bar, and a gas hourly space velocity in the range 4 to 8 $hr^{-1}$. Separation unit 117 may be used to carry out block 205-2B, which involves separating stream 115 (comprising primarily 2-butene and isobutane) into 2-butene stream 109 (comprising primarily 2-butene) and stream 119 (comprising primarily isobutane). In embodiments of the invention, separation unit 117 comprises one or more distillation columns. In embodiments of the invention, stream 115 comprises 0.01 to 70 wt. % 2-butene and 0.01 to 50 wt. % isobutane.

At block 205-3, stream 112 may be processed, in processing subunit 122 to produce 1-butene stream 108, which comprises primarily 1-butene and stream 120, a high purity stream that comprises primarily n-butane. In embodiments of the invention, stream 108 comprises 90 to 99.9 wt. % 1-butene. In embodiments of the invention, stream 120 comprises 90 to 99.9 wt. % n-butane.

Processing subunit 122 may comprise butene isomerization unit (BIU) 114 (which comprises an isomerization reactor) and separation unit 118. In embodiments of the invention, the reaction conditions in butene isomerization unit 114 include a temperature in the range 50 to 750° C., a pressure in the range 0.5 to 50 bar, and a weight hourly space velocity in the range 1 to 10 $hr^{-1}$. Butene isomerization unit 114 may be used to implement block 205-3A, which involves isomerizing the 2-butene of stream 112 (comprising primarily 2-butene and n-butane, collectively) to form 1-butene of stream 116 (comprising primarily 1-butene and n-butane, collectively). Butene isomerization unit 114 may include three reactor stages. The first two reactor stages may contain the same catalyst. The third stage reactor may contain a different catalyst.

Separation unit 118 may be used to carry out block 205-3B, which involves separating stream 116 (comprising primarily 1-butene and n-butane, collectively) into 1-butene stream 108 (comprising primarily 1-butene) and stream 120 (comprising primarily n-butane). In embodiments of the invention, separation unit 118 comprises one or more distillation columns. In embodiments of the invention, stream 116 comprises 0.01 to 70 wt. % 1-butene and 0.01 to 50 wt. % n-butane.

Block 206 of method 20 involves flowing 2-butene stream 109 to olefins conversion technology unit 123. Likewise, block 207 involves flowing 1-butene stream 108 to olefins conversion technology unit 123. At olefins conversion technology unit 123, block 208 involves converting 1-butene of 1-butene stream 108 to 2-butene. At block 208, 2-butene in olefins conversion technology unit 123 (e.g., 2-butene from 2-butene stream 109 and/or 2-butene converted from 1-butene stream 108) is reacted with ethylene 124 to produce propylene 131.

In embodiments of the invention, olefins (e.g., 1-butene and/or 2-butene) may be separated from effluent 102 and recycled to steam cracking (cracker) unit 126.

In embodiments of the invention, stream 119 (comprising primarily isobutane) from processing subunit 121 (hydro-isomerization unit 113) may be used as feedstock for a selection from the following list: a dehydrogenation unit of MTBE synthesis unit 103 and a transfer hydrogenation unit (THU) of steam cracking unit 126 to produce ethylene and propylene. When isobutane is dehydrogenated in the isobutane dehydrogenation unit of MTBE synthesis unit 103, this process provides an increase in isobutylene available for reaction to produce MTBE.

Likewise, in embodiments of the invention, stream 120 (comprising primarily n-butane) from processing subunit 122 (butene isomerization unit 114) may be used as feedstock for a selection from the following list: an isomerization unit of MTBE synthesis unit 103 and a transfer hydrogenation unit (THU) of steam cracking unit 126 to produce ethylene and propylene. The isomerization of MTBE synthesis unit 103 isomerizes the n-butane to form isobutane; this process provides an increase in isobutane, which in turn can be used as feed to the dehydrogenation unit to form isobutylene and thereby make more isobutylene available for reaction to produce MTBE.

The additional production of MTBE resulting from the isomerizing of the additional n-butane from butene isomerization unit 114 fed to the isomerizing unit and the additional isobutane from hydro-isomerizing unit 113 fed to the dehydrogenating unit, as described above, can maximize MTBE production from the steam cracker recycle stream and integrate two different systems/processes, namely MTBE system/process and steam cracker system/process.

In embodiments of the invention, purge stream 127 is combined with stream 119, and stream 120 to form combined stream 128, which may be fed to steam cracking unit 126. Steam cracking unit 126 cracks hydrocarbons of the streams it receives to produce olefins 130. In embodiments of the invention, stream 129 is recycled from steam cracking unit 126 and fed to selective hydrogenation unit 101 along with crude C$_4$ stream 100.

In view of the processing described with respect to processing unit 107, the conversion of butadiene to 1-butene and 2-butene, previously described, can increase substantially the available 2-butene stream available for olefins conversion technology unit 123 and thereby maximize the amount of propylene produced.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing methyl tertiary butyl ether (MTBE) and propylene, the method comprising:
    flowing a crude C$_4$ stream comprising butadiene, isobutylene, 2-butene, 1-butene, acetylene, isobutane, and n-butane to a selective hydrogenation unit;
    hydrogenating the butadiene in the selective hydrogenation unit to form additional 1-butene and additional 2-butene, wherein the additional 1-butene and the additional 2-butene and unreacted material of the crude C$_4$ stream is included in effluent of the selective hydrogenation unit;
    flowing the effluent of the selective hydrogenation unit to a MTBE synthesis unit;
    reacting, in the MTBE synthesis unit, the isobutylene from the crude C$_4$ stream with methanol (MeOH) to produce the MTBE,
    flowing, from the MTBE synthesis unit, a byproduct stream comprising 1-butene, isobutane, 2-butene, and n-butane to a processing unit;
    processing, in the processing unit, the byproduct stream to produce a first stream comprising primarily 1-butene and a second stream comprising primarily 2-butene;
    flowing the second stream comprising primarily 2-butene to an olefins conversion technology unit; and
    reacting the 2-butene with ethylene to produce propylene.

2. The method of claim 1 further comprising:
    hydrogenating the butadiene in the selective hydrogenation unit to form additional isobutane and additional n-butane; and
    wherein conversion of butadiene to other hydrocarbons in the selective hydrogenation unit is in a range of 88 wt. % to 92 wt. %.

3. The method of claim 1, wherein processing, in the processing unit, comprises:
    distilling, in a distillation column of the processing unit, the byproduct stream to form a first intermediate stream comprising primarily 1-butene and isobutane, collectively, and a second intermediate stream comprising primarily 2-butene and n-butane, collectively.

4. The method of claim 3, further comprising:
    processing the first intermediate stream to produce a stream comprising primarily 2-butene and a stream comprising primarily isobutane.

5. The method of claim 4, wherein the processing of the first intermediate stream comprises:
    hydro-isomerizing, in a hydro-isomerization unit, of the 1-butene in the first intermediate stream to produce a stream comprising primarily 2-butene and isobutane, collectively; and
    separating the stream comprising primarily 2-butene and isobutane into the stream comprising primarily 2-butene and the stream comprising primarily isobutane.

6. The method of claim 5, further comprising:
    flowing the stream comprising primarily 2-butene to the olefins conversion technology unit.

7. The method of claim 3, further comprising:
    processing the second intermediate stream to form a stream comprising primarily 1-butene and a stream comprising primarily n-butane.

8. The method of claim 7, wherein the processing the second intermediate stream comprises:
    isomerizing the 2-butene of the second intermediate stream to form a stream comprising primarily 1-butene and n-butane, collectively; and
    separating the stream comprising primarily 1-butene and n-butane to form the stream comprising primarily 1-butene and the stream comprising primarily n-butane.

9. The method of claim 8, further comprising:
    flowing the stream comprising primarily 1-butene to the olefins conversion technology unit;
    converting 1-butene of the stream comprising primarily 1-butene to 2-butene in the olefins conversion technology unit.

10. The method of claim 1, wherein the acetylene in the crude C4 stream comprises ethyl acetylene and vinyl acetylene.

11. The method of claim 1, wherein the butadiene comprises 1,3-butadiene and 1,2-butadiene.

12. The method of claim 5, wherein reaction conditions in hydro-isomerization unit 113 include a temperature in the range 110 to 300° C., a pressure in the range 15 to 30 bar, and a gas hourly space velocity in the range 4 to 8 hr$^1$.

13. The method of claim 8, wherein the stream comprising primarily 1-butene comprises 90 to 99.9 wt. % 1-butene.

14. The method of claim 1, wherein the crude C4 stream is at least a portion of effluent from a fluid catalytic cracking unit or steam cracking unit.

15. The method of claim 14 wherein the stream comprising primarily isobutane is used as feedstock for a selection from the list consisting of: (1) a dehydrogenation unit of the MTBE synthesis unit to produce additional isobutylene and (2) a transfer hydrogenation unit (THU) of the steam cracking unit to produce ethylene and propylene.

16. The method of claim 15, wherein the additional isobutylene is used to produce MTBE.

17. The method of claim 14, wherein the stream comprising primarily n-butane is used as feedstock for a selection from the list consisting of: (1) an isomerization unit of the MTBE synthesis unit to produce more isobutane, (2) a transfer hydrogenation unit (THU) of the steam cracking unit to produce ethylene and propylene.

18. The method of claim 13, wherein the stream comprising primarily n-butane comprises 90 to 99.9 wt. % n-butane.

19. The method of claim 5, wherein a purge stream is combined with the stream comprising primarily isobutane and the stream comprising primarily n-butane to form combined stream, which may be fed to a steam cracking unit.

20. A method of producing methyl tertiary butyl ether (MTBE) and propylene, the method consisting of the steps of:

flowing a crude $C_4$ stream comprising butadiene, isobutylene, 2-butene, 1-butene, acetylene, isobutane, and n-butane to a selective hydrogenation unit;

hydrogenating the butadiene in the selective hydrogenation unit to form additional 1-butene and additional 2-butene, wherein the additional 1-butene and the additional 2-butene and unreacted material of the crude $C_4$ stream is included in effluent of the selective hydrogenation unit;

flowing the effluent of the selective hydrogenation unit to a MTBE synthesis unit;

reacting, in the MTBE synthesis unit, the isobutylene from the crude $C_4$ stream with methanol (MeOH) to produce the MTBE, flowing, from the MTBE synthesis unit, a byproduct stream comprising 1-butene, isobutane, 2-butene, and n-butane to a processing unit;

processing, in the processing unit, the byproduct stream to produce a first stream comprising primarily 1-butene and a second stream comprising primarily 2-butene;

flowing the second stream comprising primarily 2-butene to an olefins conversion technology unit; and reacting the 2-butene with ethylene to produce propylene.

* * * * *

UNITED STATES PATENT AND TRADEMARK OFFICE
CERTIFICATE OF CORRECTION

PATENT NO. : 11,124,470 B2  
APPLICATION NO. : 16/496511  
DATED : September 21, 2021  
INVENTOR(S) : Guillermo Leal et al.

Page 1 of 1

It is certified that error appears in the above-identified patent and that said Letters Patent is hereby corrected as shown below:

In the Claims

At Column 10, Claim number 12, Line number 54, delete "hr$^1$" and replace with --hr$^{-1}$--.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*